US006020182A

United States Patent [19]
Cates et al.

[11] Patent Number: 6,020,182
[45] Date of Patent: Feb. 1, 2000

[54] SUBUNIT RESPIRATORY SYNCYTIAL VIRUS VACCINE PREPARATION

[75] Inventors: George A. Cates, Richmond Hill; Sonia E. Sanhueza, Willowdale; Raymond P. Oomen, Schomberg; Michel H. Klein, Willowdale, all of Canada

[73] Assignee: Connaught Laboratories Limited, Willowdale, Calif.

[21] Appl. No.: 08/679,060

[22] Filed: Jul. 12, 1996

[51] Int. Cl.$^7$ .............................. C12N 7/00; C12N 7/04; A61K 39/155
[52] U.S. Cl. ................... 435/235.1; 435/239; 435/236; 424/211.1
[58] Field of Search ............................ 530/350, 388.3, 530/389.1, 403; 435/5, 69.1, 69.3, 235.1, 236, 239; 536/23.72; 935/34; 424/184.1, 204.1, 211.1

[56] References Cited

FOREIGN PATENT DOCUMENTS

WO 87 04185  7/1987  WIPO .
WO 91 00104  1/1991  WIPO .
WO 94 27636  12/1994  WIPO .

OTHER PUBLICATIONS

Ewasyshyn, M.E. and Klein, M.H.; "Prospects for Immunization against Respiratory Syncytial Virus" Vaccine Research, vol. 2, 1993, pp. 263–272, XP002044888.

Walsh, E.E. et al: "Purification and Characterization of the Respiratory Syncytial Virus Fusion Protein" The Journal of General Virology, vol. 66, 1985, pp. 409–416 XP002044889.

Randolph et al. "Attenuated temperature sensitive respiratory syncitial virus mutant generated by cold adaptation". Virus Research, vol.33:241–259, 1994.

Murphy et al. "An update on approaches to the development of respiratory syncitial viral (RSV) and parainfluenza virus type 3 (PIV3) vaccines". Virus Research, vol. 32:13–36, 1994.

Wathen et al. "Characterization of a Novel Respiratory Syncitial Virus Chimeric FG Glycoprotein Expressed Using a Baculovirus Vector". J. Gen. Virology. vol.70:2625–2635, 1989.

Peretz et al. "Comparison of the ability of formalin–inactivated respiratory syncitial virus, immunopurified F, G and N proteins and cell lysate to enhance pulmonary changes in Balb/c mice". Vaccine, vol. 10, Issue 2, pp. 113–118, 1992.

Levine et al. "The Envelope Proteins from Purified Respiratory Syncytial Virus Protect Mice from Intranasal Virus Challenge". Proceedings of the Society for Experimental Biology and Medicine, vol.190, No.4:349–56, Apr. 1989.

Alansari et al. "Molecular cloning and sequence analysis of the phosphoprotein, nucleocapsid protein, matrix protein and 22K (M2) protein of the ovine respiratory syncitial virus". J. Gen. Virology, vol.75:3597–3601, 1994.

*Primary Examiner*—Mary E. Mosher
*Attorney, Agent, or Firm*—Sim & McBurney

[57] ABSTRACT

The fusion (F) protein, attachment (G) protein and matrix (M) protein of respiratory syncytial virus (RSV) are isolated and purified from respiratory syncytial virus by mild detergent extraction of the proteins from concentrated virus, loading the protein onto a hydroxyapatite or other ion-exchange matrix column and eluting the protein using mild salt treatment. The F, G and M proteins, formulated as immunogenic compositions, are safe and highly immunogenic and protect relevant animal models against respiratory syncytial virus.

15 Claims, 3 Drawing Sheets

Figure 1 - SDS-PAGE Analysis of RSV Subunit (silver stain)

(a) REDUCED

Molecular Weight x $10^{-3}$: 200, 116, 97, 66, 55, 36, 31, 21, 14

- G (95 kDa)
- $F_1$ (48 kDa)
- M (31 kDa)
- $F_2$ (23 kDa)

(b) NON-REDUCED

- F dimer
- G (95 kDa)
- $F_0$ (70 kDa)
- M (30 & 32 kDa)

Lane 1 = Molecular Weight Standards
Lane 2 = RSV Subunit

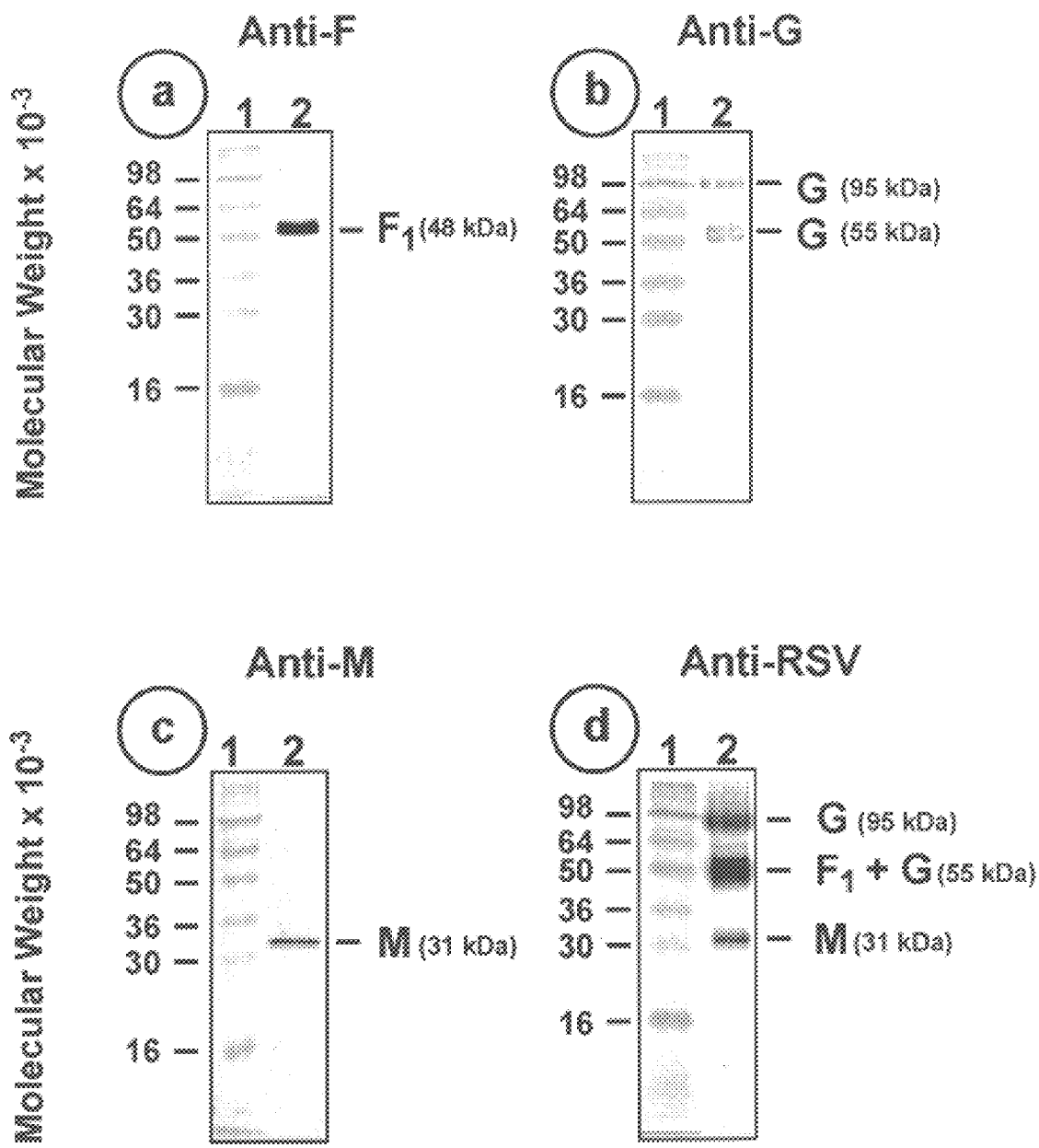

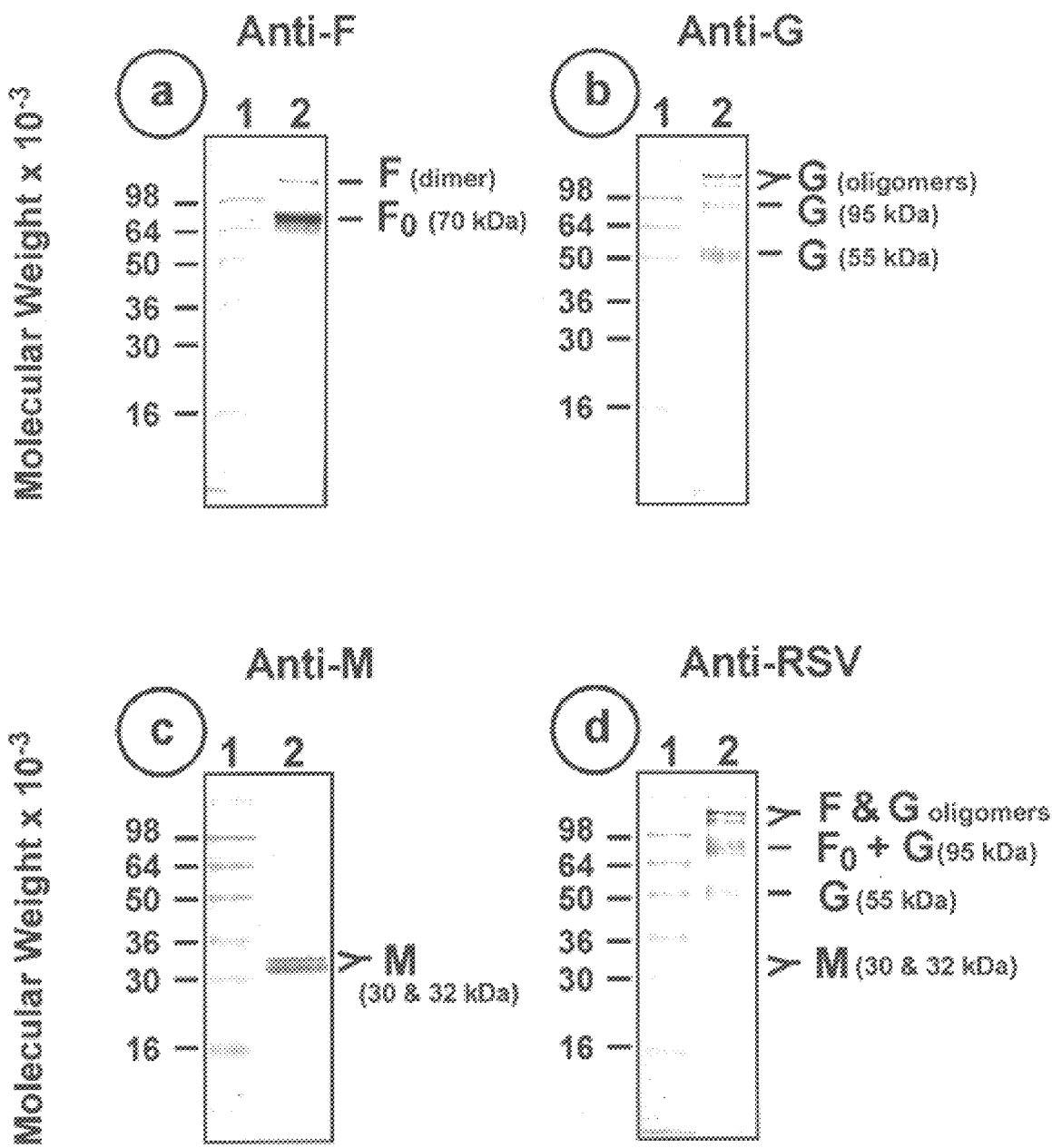
Figure 3 - Western Blot Analysis of RSV Subunit Non-Reduced
Lane 1 = Molecular Weight Standards
Lane 2 = RSV Subunit

SUBUNIT RESPIRATORY SYNCYTIAL VIRUS VACCINE PREPARATION

FIELD OF INVENTION

The present invention is related to the field of immunology and is particularly concerned with vaccine preparations against respiratory syncytial virus infection.

BACKGROUND OF THE INVENTION

Human respiratory syncytial virus is the main cause of lower respiratory tract infections among infants and young children (refs. 1 to 3—a list of references appears at the end of the disclosure and each of the references in the list is incorporated herein by reference thereto). Globally, 65 million infections occur every year resulting in 160,000 deaths (ref. 4). In the USA alone 100,000 children may require hospitalization for pneumonia and bronchiolitis caused by RS virus in a single year (refs. 5, 6). Providing inpatient and ambulatory care for children with RS virus infections costs in excess of $340 million annually in the USA (ref. 7). Severe lower respiratory tract disease due to RS virus infection predominantly occurs in infants two to six months of age (ref. 8). Approximately 4,000 infants in the USA die each year from complications arising from severe respiratory tract disease caused by infection with RS virus and Parainfluenza type 3 virus (PIV-3). The World Health Organization (WHO) and the National Institute of Allergy and Infectious Disease (NIAID) vaccine advisory committees have ranked RS virus second only to HIV for vaccine development.

The structure and composition of RSV has been elucidated and is described in detail in the textbook "Fields Virology", Fields, B. N. et al. Raven Press, N.Y. (1996), in particular, Chapter 44, pp 1313–1351 "Respiratory Syncytial Virus" by Collins, P., McIntosh, K., and Chanock, R. M. (ref. 9).

The two major protective antigens of RSV are the envelope fusion (F) and attachment (G) glycoproteins (ref. 10). The F protein is synthesized as an about 68 kDa precursor molecule ($F_0$) which is proteolytically cleaved into disulfide-linked $F_1$ (about 48 kDa) and $F_2$ (about 20 kDa) polypeptide fragments (ref. 11). The G protein (about 33 kDa) is heavily O-glycosylated giving rise to a glycoprotein of apparent molecular weight of about 90 kDa (ref. 12). Two broad subtypes of RS virus have been defined A and B (ref. 13). The major antigenic differences between these subtypes are found in the G glycoprotein while the F glycoprotein is more conserved (refs. 7, 14).

In addition to the antibody response generated by the F and G glycoproteins, human cytotoxic T cells produced by RSV infection have been shown to recognize the RSV F protein, matrix protein M, nucleoprotein N, small hydrophobic protein SH, and the nonstructural protein 1b (ref. 15).

A safe and effective RSV vaccine is not available and is urgently needed. Approaches to the development of RS virus vaccines have included inactivation of the virus with formalin (ref. 16), isolation of cold-adapted and/or temperature-sensitive mutant viruses (ref. 17) and purified F or G glycoproteins (refs. 18, 19, 20). Clinical trial results have shown that both live attenuated and formalin-inactivated vaccines failed to adequately protect vaccines against RS virus infection (refs. 21 to 23). Problems encountered with attenuated cold-adapted and/or temperature-sensitive RS virus mutants administered intranasally included clinical morbidity, genetic instability and overattenuation (refs. 24 to 26). A live RS virus vaccine administered subcutaneously also was not efficacious (ref. 27). Inactivated RS viral vaccines have typically been prepared using formaldehyde as the inactivating agent. Murphy et al. (ref. 28) have reported data on the immune response in infants and children immunized with formalin-inactivated RS virus. Infants (2 to 6 months of age) developed a high titre of antibodies to the F glycoprotein but had a poor response to the G protein. Older individuals (7 to 40 months of age) developed titres of F and G antibodies comparable to those in children who were infected with RS virus. However, both infants and children developed a lower level of neutralizing antibodies than did individuals of comparable age With natural RS virus infections. The unbalanced immune response, with high titres of antibodies to the main immunogenic RS virus proteins F (fusion) and G (attachment) proteins but a low neutralizing antibody titre, may be in part due to alterations of important epitopes in the F and G glycoproteins by the formalin treatment. Furthermore, some infants who received the formalin-inactivated RS virus vaccine developed a more serious lower respiratory tract disease following subsequent exposure to natural RS virus than did non-immunized individuals (refs. 22, 23). The formalin-inactivated RS virus vaccines, therefore, have been deemed unacceptable for human use.

Evidence of an aberrant immune response also was seen in cotton rats immunized with formalin-inactivated RS virus (ref. 29). Furthermore, evaluation of RS virus formalin-inactivated vaccine in cotton rats also showed that upon live virus challenge, immunized animals developed enhanced pulmonary histopathology (ref. 30).

The mechanism of disease potentiation caused by formalin-inactivated RS virus vaccine preparations remains to be defined but is a major obstacle in the development of an effective RS virus vaccine. The potentiation may be partly due to the action of formalin on the F and G glycoproteins. Additionally, a non-RS virus specific mechanism of disease potentiation has been suggested, in which an immunological response to contaminating cellular or serum components present in the vaccine preparation could contribute, in part, to the exacerbated disease (ref. 31). Indeed, mice and cotton rats vaccinated with a lysate of HEp-2 cells developed a heightened pulmonary inflammatory response.

Furthermore, RS virus glycoproteins purified by immunoaffinity chromatography using elution at acid pH were immunogenic and protective but also induced immunopotentiation in cotton rats (refs. 29, 32).

There clearly remains a need for immunogenic preparations, including vaccines, which are not only effective in conferring protection against disease caused by RSV but also do not produce unwanted side-effects, such as immunopotentiation. There is also a need for antigens for diagnosing RSV infection and immunogens for the generation of antibodies (including monoclonal antibodies) that specifically recognize RSV proteins for use, for example, in diagnosis of disease caused by RS virus.

SUMMARY OF THE INVENTION

The present invention provides the production of respiratory syncytial virus (RSV) on a vaccine quality cell line, for example, VERO, MRC5 or WI38 cells, purification of the virus from fermentor harvests, extraction of the F, G and M proteins from the purified virus and copurification of the F, G and M proteins without involving immunoaffinity or lentil lectin or concanavalin A affinity steps. In particular, the lectin affinity procedure, described, for example, in WO 91/00104, could lead to leaching of the ligand into the product.

In addition, there is provided herein, for the first time, a procedure for the coisolation and copurification of the F, G and M proteins of RSV and also immunogenic compositions comprising copurified mixtures of the RSV proteins.

The coisolated and copurified F, G and M RSV proteins are non-pyrogenic, non-immunopotentiating, and substantially free of serum and cellular contaminants. The isolated and purified proteins are immunogenic, free of any infectious RSV and other adventitious agents.

Accordingly, in one aspect of the present invention, there is provided a mixture of purified fusion (F) protein, attachment (G) protein and matrix (M) protein of respiratory syncytial virus (RSV).

The fusion (F) protein may comprise multimeric fusion (F) proteins, which may include, when analyzed under non-reducing conditions, heterodimers of molecular weight approximately 70 kDa and dimeric and trimeric forms.

The attachment (G) protein may comprise, when analyzed under non-reducing conditions, oligomeric G protein, G protein of molecular weight approximately 95 kDa and G protein of molecular weight approximately 55 kDa.

The matrix (M) protein may comprise, when analyzed under non-reducing conditions, protein of molecular weight approximately 28 to 34 kDa.

The protein mixture provided herein, when analyzed by reduced SDS-PAGE analysis, may comprise the fusion (F) protein comprising $F_1$ of molecular weight approximately 48 kDa and $F_2$ of about 23 kDa, the attachment (G) protein comprising a G protein of molecular weight approximately 95 kDa and a G protein of molecular weight approximately 55 kDa, and the matrix (M) protein comprising an M protein of approximately 31 kDa.

The mixture provided in accordance with this aspect of the invention may comprise the F, G and M proteins in the relative proportions of:

F about 40 to about 70 wt %
G about 5 to about 20 wt %
M about 20 to about 40 wt %

When analyzed by SDS-PAGE under reducing conditions and densitometric scanning following silver staining, the ration of $F_1$ of molecular weight approximately 48 kDa to $F_2$ of molecular weight approximately 23 kDa in this mixture may be approximately between 1:1 and 2:1. The mixture of G, G and M proteins may have a purity of at least about 75%, preferably at least about 85%.

The mixture provided herein in accordance with this aspect of the invention, having regard to the method of isolation employed herein as described below, is devoid of monoclonal antibodies and devoid of lentil lectin and concanavalin A.

The RSV proteins provided in the mixture of proteins provided herein generally are substantially non-denatured by the mild conditions of preparation and may comprise RSV proteins from one or both of subtypes RSV A and RSV B.

In accordance with a preferred embodiment of the invention, there is provided a coisolated and copurified mixture of non-denatured proteins of respiratory syncytial virus (RSV), consisting essentially of the fusion (F) protein, attachment (G) protein and matrix (M) protein of RSV, wherein the mixture is free from lentil-lectins including concanavalin A and from monoclonal antibodies.

In accordance with another aspect of the present invention, there is provided an immunogenic preparation comprising an immunoeffective amount of the mixtures provided herein.

The immunogenic compositions provided herein may be formulated as a vaccine containing the F, G and M proteins for in vivo administration to a host, which may be a primate, specifically a human host, to confer protection against disease caused by RSV.

The immunogenic compositions of the invention may be formulated as microparticles, capsules, ISCOMs or liposomes. The immunogenic compositions may further comprise at least one other immunogenic or immunostimulating material, which may be at least one adjuvant or at least one immunomodulator such as cytokines including ILK.

The at least one adjuvant may be selected from the group consisting of aluminum phosphate, aluminum hydroxide, QS21, Quil A or derivatives or components thereof, calcium phosphate, calcium hydroxide, zinc hydroxide, a glycolipid analog, an octodecyl ester of an amino acid, a muramyl dipeptide, polyphosphazene, a lipoprotein, ISCOM matrix, DC-Chol, DDA, and other adjuvants and bacterial toxins, components and derivatives thereof as for example, described in U.S. Ser. No. 08/258,228 filed Jun. 10, 1994, assigned to the assignee hereof and the disclosure of which is incorporated herein by reference thereto. Under particular circumstances, adjuvants that induce a Th1 response are desirable.

The immunogenic compositions provided herein may be formulated to comprise at least one additional immunogen, which conveniently may comprise a human parainfluenza virus (PIV) protein from PIV-1, PIV-2 and/or PIV-3 such as F and HN proteins. However, other immunogens, such as from Chlamydia, polio, hepatitis B, diphtheria toxoid, tetanus toxoid, influenza, haemophilus, B. pertussis, pneumococci, mycobacteria, hepatitis A and Moraxella also may be incorporated into the compositions, as polyvalent (combination) vaccines.

An additional aspect of the present invention provides a method of generating an immune response in a host by administering thereto an immunoeffective amount of the immunogenic composition provided herein. Preferably, the immunogenic composition is formulated as a vaccine for in vivo administration to the host and the administration to the host, including humans, confers protection against disease caused by RSV. The immune response may be humoral or a cell-mediated immune response.

The present invention provides, in an additional aspect thereof, a method of producing a vaccine for protection against disease caused by respiratory syncytial virus (RSV) infection, comprising administering the immunogenic composition provided herein to a test host to determine the amount of and frequency of administration thereof to confer protection against disease caused by a RSV; and formulating the immunogenic composition in a form suitable for administration to a treated host in accordance with the determined amount and frequency of administration. The treated host may be a human.

A further aspect of the invention provides a method of determining the presence in a sample of antibodies specifically reactive with an F, G or M protein of respiratory syncytial virus (RSV), comprising the steps of:

(a) contacting the sample with the mixture as provided herein to produce complexes comprising a respiratory syncytial virus protein and any said antibodies present in the sample specifically reactive therewith; and (b) determining production of the complexes.

In a further aspect of the invention, there is provided a method of determining the presence in a sample of a F, G or M protein of respiratory syncytial virus (RSV) comprising the steps of:

(a) immunizing a subject with the immunogenic composition as provided herein, to produce antibodies specific for the F, G and M proteins of RSV;

(b) contacting the sample with the antibodies to produce complexes comprising any RSV protein present in the sample and the protein specific antibodies; and (c) determining production of the complexes.

A further aspect of the invention provides a diagnostic kit for determining the presence of antibodies in a sample specifically reactive with a F, G or M protein of respiratory syncytial virus, comprising:

(a) a mixture as provided herein;

(b) means for contacting the mixture with the sample to produce complexes comprising a respiratory syncytial virus protein and any said antibodies present in the sample; and (c) means for determining production of the complexes.

In an additional aspect of the invention, there is provided a method of producing monoclonal antibodies specific for F, G or M proteins of respiratory syncytial virus (RSV), comprising;

(a) administrating an immunogenic composition as provided herein to at least one mouse to produce at least one immunized mouse, (b) removing B-lymphocytes from the at least one immunized mouse;

(c) fusing the B-lymphocytes from the at least one immunized mouse with myeloma cells, thereby producing hybridomas;

(d) closing the hybridomas which produce a selected anti-RSV protein antibody;

(e) culturing the selected anti-RSV protein antibody-producing clones; and (f) isolating anti-RSV protein antibodies from the selected cultures.

The present invention, in a further aspect, provides a method of producing a coisolated and copurified mixture of proteins of respiratory syncytial virus, which comprises growing RSV on cells in a culture medium, separating the grown virus from the culture medium, solubilizing at least the F, G and M proteins from the separated virus; and coisolating and copurifying the solubilized RSV proteins.

The coisolation and copurification may be effected by loading the solubilized proteins onto an ion-exchange matrix preferably a calcium phosphate matrix, specifically a hydroxyapatite matrix, and selectively coeluting the F, G and M proteins from the ion-exchange matrix. The grown virus may first be washed with urea to remove contaminants without substantially removing F, G and M proteins.

Advantages of the present invention include:

coisolated and copurified mixtures of F, G and M proteins of RSV;

immunogenic compositions containing such proteins;

procedures for isolating such protein; and diagnostic kits for identification of RSV and hosts infected thereby.

BRIEF DESCRIPTION OF DRAWINGS

FIG. 1, containing panels a and b, shows SDS-PAGE analysis of a purified RSV subunit preparation using acrylamide gels stained with silver, under both reducing (panel (a)) and non-reducing (panel (b)) conditions;

FIG. 2, containing panels a, b, c and d, shows Western blot analysis of a purified RSV subunit preparation under reducing conditions; and FIG. 3, containing panels a, b, c and d, shows Western blot analysis of a purified RSV subunit preparation under non-reducing conditions.

GENERAL DESCRIPTION OF INVENTION

As discussed above, the present invention provides the F, G and M proteins of RSV coisolated and copurified from RS virus. The virus is grown on a vaccine quality cell line, such as VERO cells and human diploid cells, MRC5 , WI38, and the grown virus is harvested. The fermentation may be effected in the presence of fetal bovine serum (FBS) and trypsin.

The viral harvest is filtered and then concentrated, typically using tangential flow ultrafiltration with a membrane of desired molecular weight cut-off and diafiltered. The virus harvest concentrate may be centrifuged and the supernatant discarded. The pellet following centrifugation may first be washed with a buffer containing urea to remove soluble contaminants while leaving the F, G and M proteins substantially unaffected, and then recentrifuged. The pellet from the centrifugation then is detergent extracted to solubilize the F, G and M proteins from the pellet. Such detergent extraction may be effected by resuspending the pellet to the original harvest concentrate volume in an extraction buffer containing a detergent, such as a non-ionic detergent, including TRITON® X-100, a non-ionic detergent which is octadienyl phenol (ethylene glycol)$_{10}$. Other detergents include octylglucoside and Mega detergents.

Following centrifugation to remove non-soluble proteins, the F, G and M protein extract is purified by chromatographic procedures. The extract may first be applied to an ion exchange chromatography matrix to permit binding the F, G and M proteins to the matrix while impurities are permitted to flow through the column. The ion-exchange chromatography matrix may be any desired chromatography material, particularly a calcium phosphate matrix, specifically hydroxyapatite, although other materials, such as DEAE and TMAE and others, may be used.

The bound F, G and M proteins then are coeluted from the column by a suitable eluant. The resulting copurified F, G and M proteins may be further processed to increase the purity thereof.

The purified F, G and M proteins employed herein may be in the form of homo and hetero oligomers including F:G heterodimers and including dimers, tetramers and higher species. The RSV protein preparations prepared following this procedure demonstrated no evidence of any adventitious agent, hemadsorbing agent or live virus.

Groups of cotton rats were immunized intramuscularly with the preparations provided herein in combination with alum or Iscomatrix™ as adjuvant. Strong anti-fusion and neutralization titres were obtained, as shown in Tables 1 and 2 below. Complete protection against virus infection was obtained in the upper and lower respiratory tracts, as shown in Tables 3 and 4 below.

In addition, groups of mice were immunized intramuscularly with the preparation provided herein in combination with alum or Iscomatrix™ as adjuvant. Strong neutralizing and anti-F antibody titres were obtained, as shown in Tables 5 and 6 below. In addition, complete protection against virus infection was obtained, as shown by the absence of virus in lung homogenates (Table 7 below).

Groups of monkeys also were immunized with the preparations provided herein in combination with alum or Iscomatrix™ as adjuvant. Strong neutralizing titres and anti-F antibody titres were obtained, as shown in Tables 8 and 9 below.

The animal immunization data generated herein demonstrate that, by employing mild detergent extraction of the major RSV proteins from virus and mild salt elution of the proteins from the ion-exchange matrix, there is obtained copurified mixtures of the F, G and M RSV proteins which is capable of eliciting an immune response in experimental animals models that confers protection against RSV challenge.

The invention extends to the mixture of F, G and M proteins from respiratory syncytial virus for use as a pharmaceutical substance as an active ingredient in a vaccine against disease caused by infection with respiratory syncytial virus.

In a further aspect, the invention provides the use of F, G and M proteins from respiratory syncytial virus for the preparation of a vaccinal composition for immunization against disease caused by infection with respiratory syncytial virus.

It is clearly apparent to one skilled in the art, that the various embodiments of the present invention have many applications in the fields of vaccination, diagnosis and treatment of respiratory syncytial virus infections, and the generation of immunological agents. A further non-limiting discussion of such issue is further presented below.

1. Vaccine Preparation and Use

Immunogenic compositions, suitable to be used as vaccines, may be prepared from mixtures comprising immunogenic F, G and M proteins of RSV as disclosed herein. The immunogenic composition elicits an immune response which produces antibodies, including anti-RSV antibodies including anti-F, anti-G and anti-M antibodies. Such antibodies may be viral neutralizing and/or anti-fusion antibodies.

Immunogenic compositions including vaccines may be prepared as injectables, as liquid solutions, suspensions or emulsions. The active immunogenic ingredient or ingredients may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneous, intradermal or intramuscularly injection. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active immunogenic ingredient (s) in the range of about 0.5 to about 10%, preferably about 1 to 2%. Oral formulations may include normally employed carriers such as, pharmaceutical grades of saccharine, cellulose and magnesium carbonate. These compositions can take the form of solutions, suspensions, tablets, pills, capsules, sustained release formulations or powders and contain about 1 to 95% of the active ingredient (s), preferably about 20 to about 75%.

The immunogenic preparations and vaccines are administered in a manner compatible with the dosage formulation, and in such amount as will be therapeutically effective, immunogenic and protective. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms to milligrams of the active ingredient(s) per vaccination. Suitable regimes for initial administration and booster doses are also variable, but may include an initial administration followed by subsequent booster administrations. The dosage may also depend or the route of administration and will vary according to the size of the host.

The concentration of the active ingredient protein in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens. In the present invention, as noted above, F, G and M proteins of RSV A and RSV B are combined in a single multivalent immunogenic composition which also may contain other immunogens.

Immunogenicity can be significantly improved if the antigens are co-administered with adjuvants. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and usually does not elicit a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's incomplete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

2. Immunoassays

The F, G and M proteins of RSV of the present invention are useful as immunogens for the generation of antibodies thereto, as antigens in immunoassays including enzyme-linked immunosorbent assays (ELISA), RIAs and other non-enzyme linked antibody binding assays or procedures known in the art for the detection of antibodies. In ELISA assays, the selected F, G or M protein or a mixture of proteins is immobilized onto a selected surface, for example, a surface capable of binding proteins such as the wells of a polystyrene microtiter plate. After washing to remove incompletely adsorbed material, a nonspecific protein, such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific binding of proteins in the antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures, such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then be achieved by measuring the degree of color generation using, for example, a spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of determining tissue culture infectious dose$_{50}$ (TCID$_{50}$/mL), plaque and neutralization titres, not explicitly described in this disclosure are amply reported in the scientific literature and well within the scope of those skilled in the art. Protein concentrations were determined by the bicinchoninic acid (BCA) method as described in the Pierce Manual (23220, 23225; Pierce Chemical Company, U.S.A.), incorporated herein by reference.

CMRL 1969 culture medium was used for cell culture and virus growth. The cells used in this study are vaccine quality African green monkey kidney cells (VERO lot M6) obtained from Institut Merieux. The RS viruses used were the RS virus subtype A (Long and A2 strains) obtained from the American Type culture Collection (ATCC) and a recent subtype A clinical isolate.

Example 1

This Example illustrates the production of RSV on a mammalian cell line on microcarrier beads in a 150 L controlled fermenter.

Vaccine quality African Green monkey kidney cells (VERO) at a concentration of $10^5$ cells/mL were added to 60 L of CMRL 1969 medium, pH 7.2 in a 150 L bioreactor containing 360 g of Cytodex-1 microcarrier beads and stirred for 2 hours. An additional 60 L of CMRL 1969 was added to give a total volume of 120 L. Fetal bovine serum was added to achieve a final concentration of 3.5%. Glucose was added to a final concentration of 3 g/L and L-glutamine was added to a final concentration of 0.6 g/L. Dissolved oxygen (40%), pH (7.2), agitation (36 rpm), and temperature (37° C.) were controlled. Cell growth, glucose, lactate, and glutamine levels were monitored. At day 4, the culture medium was drained from the fermenter and 100 L of E199 media (no fetal bovine serum) was added and stirred for 10 minutes. The fermentor was drained and filled again with 120 L of E199. The RSV inoculum was added at a multiplicity of infection (M.O.I.) of 0.001 and the culture was then maintained for 3 days before one-third to one-half of the medium was drained and replaced with fresh medium. On day 6 post-infection, the stirring was stopped and the beads allowed to settle. The viral culture fluid was drained and filtered through a 20 µm filter followed by a 3 µm filter prior to further processing.

The clarified viral harvest was concentrated 75- to 150-fold using tangential flow ultrafiltration with 300 NMWL membranes and diafiltered with phosphate buffered saline containing 10% glycerol. The viral concentrate was stored frozen at −70° C. prior to further purification.

Example 2

This Example illustrates the process of purifying RSV subunit from a viral concentrate.

A solution of 50% polyethylene glycol-8000 was added to an aliquot of virus concentrate to give a final concentration of 6%. After stirring at room temperature for one hour, the mixture was centrifuged at 15,000 RPM for 30 min in a Sorvall SS-34 rotor at 4° C. In some instances the viral pellet was suspended in 1 mM sodium phosphate, pH 6.8, 2 M urea, 0.15 M NaCl, stirred for 1 hour at room temperature, and then recentrifuged at 15,000 RPM for 30 min. in a Sorvall SS-34 rotor at 4° C. The viral pellet was then suspended in 1 mM sodium phosphate, pH 6.8, 50 mM NaCl, 1% Triton X-100 and stirred for 30 minutes at room temperature. The insoluble virus core was removed by centrifugation at 15,000 RPM for 30 min. in a Sorval SS-34 rotor at 4° C. The soluble protein supernatant was applied to a column of ceramic hydroxyapatite (type II, Bio-Rad Laboratories) and the column was then washed with five column volumes of 1 mM sodium phosphate, pH 6.8, 50 mM NaCl, 0.02% Triton X-100. The RSV subunit composition, containing the F, G and M proteins, was obtained by eluting the column with 10 column volumes of 1 mM sodium phosphate, pH 6.8, 400 mM NaCl, 0.02% Triton X-100.

Example 3

This Example illustrates the analysis of RSV subunit preparation by SDS polyacrylamide gel electrophoresis (SDS-PAGE) and by immunoblotting.

The RSV subunit preparation was analyzed by SDS-PAGE using 12.5% acrylamide gels. Samples were electrophoresed in the presence or absence of 2-mercaptoethanol (reducing agent). Gels were stained with silver stain to detect the viral proteins (FIG. 1, panels a and b). Immunoblots of replicate gels were prepared and probed with a mouse monoclonal antibody (mAb 5353C75) to F glycoprotein (FIGS. 2 panel a and 3, panel a), or a mouse monoclonal antibody (mAb 131-2G), to G glycoprotein (FIGS. 2, panel b and 3, panel b) or guinea pig anti-serum (gpl78) against an RSV M peptide (peptide sequence: LKSKNMLTTVKDLTMKTLNPTHDIIALCEFEN - SEQ ID No:1) (FIGS. 2, panel c and 3, panel c), or goat antiserum (Virostat #0605) against whole RSV (FIGS. 2, panel d and 3, panel d). Densitometric analysis of the silver-stained gel of the RSV subunit preparation electrophored under reducing conditions indicated a compositional distribution as follows:

G glycoprotein (95 kDa form)=10%

$F_1$ glycoprotein (48 kDa)=30%

M protein (31 kDa)=23%

$F_2$ glycoprotein (23 kDa)=19%

The F glycoprotein migrates under non-reducing conditions as a heterodimer of approximately 70 kDa ($F_0$) as well as higher oligomeric forms (dimers and trimers) (FIG. 3, panel a).

Example 4

This Example illustrates the immunogenicity of the RSV subunit preparation in cotton rats.

Groups of five cotton rats were immunized intramuscularly (0.1 mL on days 0 and 28 with 1 μg or 10 μg the RSV subunit preparation, produced as described in Example 2 and formulated with either 1.5 mg/dose alum or 5 μg/dose Iscomatrix™ (Iscotec, Sweden). Blood samples were obtained on day 41 and assayed for anti-fusion titres and neutralization titres. The rats were challenged intranasally on day 43 with RSV and sacrificed four days later. Lavages of the lungs and naso pharynx were collected and assayed for RSV titres. Strong anti-fusion and neutralizing antibody titres were induced as shown in Tables 1 and 2 below. In addition, complete protection against virus infection was obtained with the exception of one rat, in both the upper and lower respiratory tracts (Tables 3 and 4 below).

Example 5

This Example illustrates the immunogenicity of the RSV subunit preparation in mice.

Groups of six BALB/c mice were immunized intramuscularly (0.1 mL on days 0 and 28 with 1 μg or 10 μg of the RSV subunit preparation, produced as described in Example 2 and formulated with wither 1.5 mg/dose alum or 10 μg/dose Iscomatrix™. Blood samples were obtained on days 28 and 42 and assayed for neutralizing and anti-F antibody titres. The mice were challenged on day 44 with RSV and sacrificed four days later. Lungs were removed and homogenized to determine virus titres. Strong neutralizing and anti-F antibody titres were elicited as shown in Tables 5 and 6 below. In addition, complete protection against virus infection was obtained as shown by the absence of virus in lung homogenates and nasal washes (Table 7 below).

Example 6

This Example illustrates the immunogenicity of RSV subunit preparation in African green monkeys.

Groups of four monkeys were immunized intramuscularly (0.5 mL on days 0 and 21 with 100 μg of the RSV subunit preparation, produced as described in Example 2 and formulated with wither 1.5 mg/dose alum or 50 μg/dose Iscomatrix™. Blood samples were obtained on days 21, 35 and 49 and assayed for neutralizing and anti-F antibody titres. Strong neutralizing and anti-F antibody titres were obtained as shown in Tables 8 and 9 below.

SUMMARY OF DISCLOSURE

In summary of this disclosure, the present invention provides a coisolated and purified mixture of F, G and M proteins of RSV which is able to protect against RSV in relevant animal models of infection. Modifications are possible within the scope of this invention.

TABLE 1

Serum Anti-Fusion Titres in Cotton Rats

| Group | Mean titre ($\log_2$) | Std. Dev. ($\log_2$) |
|---|---|---|
| Alum placebo | 2.0 | 0.0 |
| Iscomatrix ™ placebo | 2.3 | 0.5 |
| RSV Subunit 1 μg with Alum | 8.0 | 1.0 |
| RSV Subunit 10 μg with Alum | 7.5 | 1.0 |
| RSV Subunit 1 μg with Iscomatrix ™ | 10.4 | 1.3 |
| RSV Subunit 10 μg with Iscomatrix ™ | 10.0 | 1.6 |

TABLE 2

Serum Nutralization Titres in Cotton Rats

| Group | Mean titre ($\log_2$) | Std. Dev. ($\log_2$) |
|---|---|---|
| Alum placebo | 2.0 | 0.0 |
| Iscomatrix ™ placebo | 2.0 | 0.0 |
| RSV Subunit 1 μg with Alum | 9.6 | 1.3 |
| RSV Subunit 10 μg with Alum | 10.0 | 1.4 |
| RSV Subunit 1 μg with Iscomatrix ™ | 10.6 | 1.1 |
| RSV Subunit 10 μg with Iscomatrix ™ | 11.2 | 1.1 |

TABLE 3

Pulmonary Wash RSV Titres in Cotton Rats

| Group | Mean titre ($\log_{10}$/g lung) | Std. Dev. ($\log_{10}$/g lung) |
|---|---|---|
| Alum placebo | 3.8 | 0.4 |
| Iscomatrix ™ placebo | 3.7 | 0.5 |
| RSV Subunit 1 μg with Alum | 0.4 | 0.8 |
| RSV Subunit 10 μg with Alum | 0.0 | 0.0 |
| RSV Subunit 1 μg with Iscomatrix ™ | 0.0 | 0.0 |
| RSV Subunit 10 μg with Iscomatrix ™ | 0.0 | 0.0 |

TABLE 4

Nasal Wash RSV Titres in Cotton Rats

| Group | Mean titre (log$_{10}$/g lung) | Std. Dev. (log$_{10}$/g lung) |
|---|---|---|
| Alum placebo | 3.2 | 0.5 |
| Iscomatrix ™ placebo | 3.1 | 0.3 |
| RSV Subunit 1 μg with Alum | 0.0 | 0.0 |
| RSV Subunit 10 μg with Alum | 0.0 | 0.0 |
| RSV Subunit 1 μg with Iscomatrix ™ | 0.0 | 0.0 |
| RSV Subunit 10 μg with Iscomatrix ™ | 0.0 | 0.0 |

TABLE 5

Serum Neutralization Titres in Balb/c Mice

| | 4 Week Bleed | | 6 Week Bleed | |
|---|---|---|---|---|
| Group | Mean titre (log$_2$) | Std. Dev. (log$_2$) | Mean titre (log$_2$) | Std. Dev. (log$_2$) |
| Alum placebo | 3.0 | 0.0 | 3.0 | 0.0 |
| Iscomatrix ™ placebo | 3.0 | 0.0 | 3.0 | 0.0 |
| RSV Subunit 1 μg with Alum | 6.5 | 0.6 | 8.7 | 1.0 |
| RSV Subunit 10 μg with Alum | 8.0 | 1.1 | 9.5 | 1.1 |
| RSV Subunit 1 μg with Iscomatrix ™ | 8.2 | 0.8 | 13.2 | 1.0 |
| RSV Subunit 10 μg with Iscomatrix ™ | 10.4 | 1.3 | 13.4 | 0.6 |

TABLE 6

Serum Anti-F Titres in Balb/c Mice

| | 4 Week Bleed | | 6 Week Bleed | |
|---|---|---|---|---|
| Group | Mean titre (log$_2$titre/100) | Std. Dev. (log$_2$titre/100) | Mean titre (log$_2$titre/100) | Std. Dev. (log$_2$titre/100) |
| Alum placebo | 0.5 | 1.2 | 0.0 | 0.0 |
| Iscomatrix ™ placebo | 1.0 | 0.0 | 0.0 | 0.0 |
| RSV Subunit 1 μg with Alum | 8.7 | 0.8 | 11.2 | 0.8 |
| RSV Subunit 10 μg with Alum | 9.7 | 0.8 | 12.3 | 1.0 |
| RSV Subunit 1 μg with Iscomatrix ™ | 8.5 | 0.6 | 13.3 | 0.5 |
| RSV Subunit 10 μg with Iscomatrix ™ | 10.0 | 0.0 | 13.0 | 0.0 |

TABLE 7

Lung Virus Titres in Balb/c Mice

| Group | Mean titre (log$_{10}$/g lung) | Std. Dev. (log$_{10}$/g lung) |
|---|---|---|
| Alum placebo | 4.1 | 0.2 |
| Iscomatrix ™ placebo | 3.5 | 0.1 |
| RSV Subunit 1 μg with Alum | 0.0 | 0.0 |
| RSV Subunit 10 μg with Alum | 0.0 | 0.0 |
| RSV Subunit 1 μg with Iscomatrix ™ | 0.0 | 0.0 |
| RSV Subunit 10 μg with Iscomatrix ™ | 0.0 | 0.0 |

TABLE 8

Serum Neutralization Titres in African Green Monkeys

| Group | 3 Week Bleed | | 5 Week Bleed | | 7 Week Bleed | |
|---|---|---|---|---|---|---|
| | Mean titre ($\log_2$) | Std. Dev. ($\log_2$) | Mean titre ($\log_2$) | Std. Dev. ($\log_2$) | Mean titre ($\log_2$) | Std. Dev. ($\log_2$) |
| Alum placebo | 3.3 | 0.0 | 3.3 | 0.0 | 3.3 | 0.0 |
| Iscomatrix ™ placebo | 3.3 | 0.0 | 3.3 | 0.0 | 3.3 | 0.0 |
| RSV Subunit 100 μg with Alum | 11.3 | 1.3 | 14.6 | 1.3 | 11.5 | 1.4 |
| RSV Subunit 100 μg with Iscomatrix ™ | 10.8 | 0.7 | 15.1 | 0.1 | 11.9 | 0.5 |

TABLE 9

Serum Anti-F Titres in African Green Monkeys

| Group | 3 Week Bleed | | 5 Week Bleed | | 7 Week Bleed | |
|---|---|---|---|---|---|---|
| | Mean titre ($\log_2$ titre/100) | Std. dev. ($\log_2$ titre/100) | Mean titre ($\log_2$ titre/100) | Std. dev. ($\log_2$ titre/100) | Mean titre ($\log_2$ titre/100) | Std. dev. ($\log_2$ titre/100) |
| Alum placebo | 0.0 | 0.0 | 0.0 | 0.0 | 0.0 | 0.0 |
| Iscomatrix ™ placebo | 0.0 | 0.0 | 0.0 | 0.0 | 0.0 | 0.0 |
| RSV Subunit 100 μg with Alum | 6.5 | 1.9 | 9.3 | 1.0 | 9.0 | 1.2 |
| RSV Subunit 100 μg with Iscomatrix ™ | 5.5 | 1.0 | 9.8 | 0.5 | 9.5 | 1.0 |

REFERENCES

1. Glezen, W. P., Parades, A. Allison, J. E., Taber, L. H. and Frank, A. L. (1981). J. Pediatr. 98, 708–715.
2. Chanock, R. M., Parrot, R. H., Connors, M., Collins, P. L. and Murphy, B. R. (1992) Pediatrics 90, 137–142.
3. Martin, A. J. Gardiner, P. S. and McQuillin, J. (1978). Lancel ii, 1035–1038
4. Robbins, A., and Freeman, P. (1988) Sci. Am. 259, 126–133.
5. Glezen, W. P., Taber, L. H., Frank, A. L. and Kasel, J. A. (1986) Am. J. Dis. Child. 140, 143–146.
6. Katz, S. L. New vaccine development establishing priorities. Vol. 1. Washington: National Academic Press. (1985) pp. 397–409.
7. Wertz, G. W., Sullender, W. M. (1992) Biotech, 20, 151–176.
8. McIntosh, K. and Chanock, R. M. (1990) in Fields Virology (Fields, B. M., and Knipe, D. M. eds.) pp. 1045–1075, Raven Press, Ltd., New York.
9. Collins, P., McIntosh, K., and Chanock, R. M. in "Fields Virology" ed. by Fields, B. N., Knipe, D. M., and Howley, P. M., Lippincott-Raven Press, New York, (1996) pp. 1313–1351.
10. Walsh, E. E., Hall, C. B., Briselli, M., Brandiss, M. W. and Schlesinger, J. J. (1987) J. Infect. Dis. 155, 1198–1204.
11. Walsh, E. E., Hruska, J. (1983) J. Virol. 47, 171–177.
12. Levine, S., Kleiber-France, R., and Paradiso, P. R. (1987) J. Gen. Virol. 69, 2521–2524.
13. Anderson, L. J. Hierholzer, J. C., Tsou, C., Hendry, R. M., Fernie, B. F., Stone, Y. and McIntosh, K. (1985), J. Infect. Dis. 151, 626–633.
14. Johnson, P. R., Olmsted, R. A., Prince, G. A., Murphy B. R., Alling, D. W., Walsh, E. E. and Collins, P. L. (1987) J. Virol. 61 (10), 3163–3166.
15. Cherrie, A. H., Anderson, K., Wertz, G. W., and Openshaw, P. J. M. (1992) J. Virology 66, 2102–2110.
16. Kim, H. W., Canchola, J. G., Brandt, C. D., Pyles, G., Chanock, R. M. Jensen, K., and Parrott, R. H. (1969) Amer. J. Epidemiology 89, 422–434.
17. Firedewald, W. T., Forsyth, B. R., Smith, C. B., Gharpure, M. S., and Chanock, R. M. (1969) JAMA 204, 690–694.
18. Walsh, E. E., Brandriss, M. W., Schlesinger, J. J. (1985) J. Gen. Virol. 66, 409–415.
19. Walsh, E. E., Schlesinger, J. J. and Brandriss, M. W. (1984) J. Gen. Virol. 65, 761–766.
20. Routledge, E. G., Willcocks, M. M., Samson, A. C. R., Morgan, L., Scott, R., Anderson, J. J., and Toms, G. L. (1988) J. Gen. Virology 69, 293–303.
21. Fulginiti, V. A., Eller, J. J., Sieber, O. F., Joyner, I. W., Minamitani, M. and Meiklejohn, G. (1969) Am J. Epidemiol. 89 (4), 435–448.
22. Chin, J., Magoffin, R. L., Shearer, L. A., Schieble, J. H. and Lennette, E. H. (1969) Am. J. Epidemiol. 89 (4), 449–463.
23. Kapikian, A. Z., Mitchell, R. H., Chanock, R. M., Shvedoff, R. A. and Stewart, C. E. (1969) Am. J. Epidemiol. 89 (4), 405–421.
24. Kim, H. W., Arrobio, J. O., Pyles, G., Brandt, C. D. Camargo, E., Chanock, R. M. and Parrott, R. H. (1971) Pediatrics 48, 745–755.
25. Wright, P. F., Belshe, R. B., Kim, H. W., Van Voris, L. P. and Chanock, r. M. 91982) Infect. Immun. 37 (1), 397–400.
26. Wright P. F., Chinozaki, T. and Fleet, W. (1976) J. Pediatr. 88, 931–936.
27. Belshe, R. B., Van Voris, P. and Mufson, M. A. (1982) J. Infect. Dis. 145, 311–319.
28. Murphy, B. R., Prince, G. A., Walsh, E. E., Kim, H. W., Parrott, R. H., Hemming V. G., Rodriguez, W. J., and Chanock, R. M.. J. Clin. Microbiol. (1986), 24(2), 197–202.
29. Connors, M., Collins, P. L., Firestone, C. Y., Sotnikov, A. V., Waitze, A., Davis, A. R., Hung, P. P., Chanock, R. M., Murphy, b. (1992) Vaccine, 10, 475–484.
30. Prince, G. A., Jenson, A. B., Hemming, V. G., Murphy, E. R., Walsh, E. E., Horswood, R. L. and Chanock, R. L. (1986b) J. Virol. 57 (3), 721–728.
31. Piedra, P. A., Cammussi, F. and Ogra, P. L. (1989) J. Gen. Virol. 70, 325–333.

32. Walsh, E. E., Hall, C. B., Briselli, M., Brandiss, M. W. and Schlesinger, J. J. (1987) J. Infect. Dis. 155 (6), 1198–1204.

What we claim is:

1. A mixture of purified fusion protein (F), attachment protein (G) and matrix (M) protein of respiratory syncytial virus in the relative proportions of:

F from about 40 to about 70 wt %

G from about 5 to about 20 wt %

M from about 20 to about 40 wt %.

2. The mixture of claim 1 wherein, when analyzed by SDS-PAGE under reducing conditions and silver stained, the ratio of $F_1$ of molecular weight approximately 48 kDa to $F_2$ of molecular weight approximately 23 kDa is between 1:1 to about 2:1 by scanning densitometry.

3. The mixture of claim 1 which is at least about 75% pure.

4. A mixture consisting essentially of purified fusion (F) protein, attachment (G) protein and matrix (M) protein of respiratory syncytial virus (RSV).

5. The mixture of claim 4 wherein said fusion (F) protein comprises multimeric fusion (F) proteins.

6. The mixture of claim 5 wherein, when analyzed under non-reducing conditions, said multimeric fusion (F) protein includes heterodimers of molecular weight approximately 70 kDa and dimeric and trimeric forms.

7. The mixture of claim 4 wherein, when analyzed under non-reducing conditions, said attachment (G) protein comprises G protein of molecular weight approximately 95 kDa and G protein of molecular weight approximately 55 kDa and oligomeric G protein.

8. The mixture of claim 4 wherein, when analyzed by SDS-PAGE under non-reducing conditions, said matrix (M) protein comprises M protein of molecular weight approximately 28 to 34 kDa.

9. The mixture of claim 4 wherein, when analyzed by reduced SDS-PAGE analysis, said fusion (F) protein comprises $F_1$ of molecular weight approximately 48 kDa and $F_2$ of molecular weight approximately 23 kDa, said attachment (G) protein comprises a G protein of molecular weight approximately 95 kDa and a G protein of molecular weight approximately 55 kDa, and said matrix (M) protein comprises an M protein of approximately 31 kDa.

10. The mixture of claim 4 which is devoid of monoclonal antibodies.

11. The mixture of claim 4 which is devoid of lentil lectin and concanavalin A.

12. The mixture of claim 4 wherein said RSV proteins are non-denatured.

13. The mixture of claim 4 wherein said RSV proteins are from one or both of subtypes RSV A and RSV B.

14. A coisolated and copurified mixture of non-denatured proteins of respiratory syncytial virus (RSV), consisting essentially of the fusion (F) protein, attachment (G) protein and matrix (M) protein of RSV, wherein the mixture is free from lectins and is free from monoclonal antibodies.

15. The mixture of claim 14 wherein said F, G and M proteins are present in the relative proportions of:

F from about 40 to about 70 wt %

G from about 5 to about 20 wt %

M from about 20 to about 40 wt %.

* * * * *

UNITED STATES PATENT AND TRADEMARK OFFICE
CERTIFICATE OF CORRECTION

PATENT NO. : 6,020,182
DATED : February 1, 2000
INVENTOR(S) : George A. Cates et al It is certified that error appears in the above-identified patent and that said Letters Patent are hereby corrected as shown below: Title page, item [73] should read --

Assignee: Connaught Laboratories Limited,
Address : Willowdale, Ontario, CA

Signed and Sealed this

Tenth Day of April, 2001

Attest:

NICHOLAS P. GODICI

Attesting Officer    Acting Director of the United States Patent and Trademark Office